US012710424B2

(12) United States Patent
Kuppili et al.

(10) Patent No.: US 12,710,424 B2
(45) Date of Patent: Aug. 18, 2026

(54) EXTRACTION PROCESS OF PANCRELIPASE AND EVALUATION THEREOF

(71) Applicant: Kashiv BioSciences, LLC, Piscataway, NJ (US)

(72) Inventors: Raja Reddy Kuppili, Thane (IN); Chintan Mineshkumar Vaywala, Ahmedabad (IN); Parva Yogeshchandra Purohit, Ahmedabad (IN); Mukesh Mahajan, Ahmedabad (IN); Sanjaykumar Vanrajbhat Talpara, Ahmedabad (IN)

(73) Assignee: Kashiv BioSciences, LLC, Piscataway, NJ (US)

( * ) Notice: Subject to any disclaimer, the term of this patent is extended or adjusted under 35 U.S.C. 154(b) by 207 days.

(21) Appl. No.: 18/262,316

(22) PCT Filed: Mar. 23, 2022

(86) PCT No.: PCT/IB2022/052651

§ 371 (c)(1),
(2) Date: Jul. 20, 2023

(87) PCT Pub. No.: WO2022/201056

PCT Pub. Date: Sep. 29, 2022

(65) Prior Publication Data

US 2024/0077483 A1 Mar. 7, 2024

(30) Foreign Application Priority Data

Mar. 23, 2021 (IN) ............................ 202121012561

(51) Int. Cl.
*C12Q 1/34* (2006.01)
*G01N 33/573* (2006.01)

(52) U.S. Cl.
CPC ....... *G01N 33/573* (2013.01); *G01N 2333/92* (2013.01)

(58) Field of Classification Search
CPC .................................................... G01N 33/573
See application file for complete search history.

(56) References Cited

U.S. PATENT DOCUMENTS

| | | | |
|---|---|---|---|
| 5,328,834 | A | 7/1994 | Ngo et al. |
| 8,703,126 | B2 | 4/2014 | Liu et al. |
| 9,291,630 | B1 | 3/2016 | Wezeman et al. |
| 9,352,035 | B2 | 5/2016 | Zhou et al. |
| 9,382,317 | B2 | 7/2016 | Manning et al. |
| 9,556,258 | B2 | 1/2017 | Nti-Gyabaah et al. |
| 9,598,718 | B2 | 3/2017 | Rupprechter et al. |
| 9,683,012 | B2 | 6/2017 | Yoon et al. |
| 10,034,940 | B2 | 7/2018 | Liu et al. |
| 10,080,793 | B2 | 9/2018 | van't Oever et al. |
| 10,618,960 | B2 | 4/2020 | Liu et al. |
| 12,139,510 | B2 | 11/2024 | Narayan et al. |
| 2002/0114814 | A1 | 8/2002 | Gray et al. |
| 2006/0228780 | A1 | 10/2006 | Luo et al. |
| 2008/0064861 | A1 | 3/2008 | Sun |
| 2008/0167450 | A1 | 7/2008 | Pan |
| 2009/0252749 | A1 | 10/2009 | Leister et al. |
| 2010/0129379 | A1 | 5/2010 | Carpenter et al. |
| 2010/0278929 | A1 | 11/2010 | Wei et al. |
| 2011/0129468 | A1 | 6/2011 | Mccue et al. |
| 2012/0172299 | A1 | 7/2012 | Schmalz et al. |
| 2012/0322733 | A1 | 12/2012 | Shaw |
| 2013/0079498 | A1 | 3/2013 | Gilljam et al. |
| 2013/0197198 | A1 | 8/2013 | Sun et al. |
| 2013/0338344 | A1 | 12/2013 | Ramasubramanyan et al. |
| 2014/0288272 | A1 | 9/2014 | Allison et al. |
| 2014/0341843 | A1 | 11/2014 | Barnes et al. |
| 2015/0284673 | A1 | 10/2015 | Langer et al. |
| 2016/0115193 | A1 | 4/2016 | Herigstad et al. |
| 2016/0228371 | A1 | 8/2016 | Schultz et al. |
| 2017/0007712 | A1 | 1/2017 | DeFrees et al. |
| 2017/0058019 | A1 | 3/2017 | Felföldi et al. |
| 2017/0305999 | A1 | 10/2017 | Leber et al. |
| 2017/0326069 | A1 | 11/2017 | Brunner-Schwarz et al. |
| 2018/0037642 | A1 | 2/2018 | Arakawa et al. |
| 2018/0208639 | A1 | 7/2018 | Minter et al. |
| 2018/0327446 | A1 | 11/2018 | Fong et al. |
| 2018/0333493 | A1 | 11/2018 | Shenoy |

(Continued)

FOREIGN PATENT DOCUMENTS

| | | | |
|---|---|---|---|
| CA | 2528906 | C | 7/2013 |
| CA | 3072129 | A1 | 3/2019 |

(Continued)

OTHER PUBLICATIONS

English Translation of CN 103667225 retrieved on Sep. 10, 2025.*
English Translation of CN 103405756 retrieved on Sep. 10, 2025.*
Aasim et al., "The role of ligands on protein retention in adsorption chromatography: A surface energetics approach", p. 618-624, Journal of Separation Science, vol. 37, Issue 6. Jan. 21, 2014.
Ahmed et al. (1992) "Biosep-SEC-S high-performance size-exclusion chromatographic columns for proteins and peptides," Journal of Chromatography 599:25-33.

(Continued)

*Primary Examiner* — Yong D Pak
(74) *Attorney, Agent, or Firm* — Goodwin Procter LLP

(57) ABSTRACT

The invention provided herein a pharmaceutical process used for an extraction of proteins from pancreatic sample and estimation of the extracted proteins. Moreover, the invention provides a use of suitable is selected from citrate-phosphate buffer and bicarbonate buffer capable to extract proteins from pancreatic sample. The invention further provides an analytical method to perform estimation of extracted proteins. This process provides an improved extraction method to quantify protein present in the pancreatic sample.

20 Claims, 10 Drawing Sheets

(56) References Cited

U.S. PATENT DOCUMENTS

2018/0344630 A1 12/2018 Igawa et al.
2019/0062419 A1 2/2019 Ramasubramanyan et al.
2019/0256556 A1 8/2019 Giese et al.
2019/0298801 A1 10/2019 Kerwin et al.
2019/0343918 A1 11/2019 Graham et al.
2019/0353661 A1 11/2019 Smith
2019/0358323 A1 11/2019 Liu et al.
2020/0003714 A1 1/2020 Gillespie et al.
2020/0017569 A9 1/2020 Leister et al.
2020/0088749 A1 3/2020 Salbato et al.
2020/0230242 A1 7/2020 Desai et al.
2020/0283472 A1 9/2020 Karur
2021/0079422 A1 3/2021 Oh et al.
2021/0122782 A1 4/2021 Eisenhuth et al.
2021/0130396 A1 5/2021 Sutter et al.
2021/0179690 A1 6/2021 Jayaraman et al.
2021/0230250 A1 7/2021 Lazar et al.
2022/0194980 A1 6/2022 Leiss et al.
2022/0203347 A1 6/2022 Wong et al.
2022/0260521 A1 8/2022 Upadhyay
2022/0267473 A1 8/2022 Weaver et al.
2023/0124565 A1 4/2023 Yang et al.
2023/0166200 A1 6/2023 Narayan et al.
2023/0166201 A1 6/2023 Narayan et al.
2023/0167153 A1 6/2023 Narayan et al.
2023/0303621 A1 9/2023 Mahajan
2023/0340080 A1 10/2023 Sharma et al.
2023/0348530 A1 11/2023 Narayan et al.
2024/0077483 A1 3/2024 Kuppili et al.
2024/0156907 A1 5/2024 Narayan et al.
2024/0158437 A1 5/2024 Narayan et al.
2024/0254160 A1 8/2024 Upadhyay et al.
2024/0287159 A1 8/2024 Sharma et al.
2024/0317799 A1 9/2024 Narayan et al.
2024/0343758 A1 10/2024 Narayan et al.
2024/0343776 A1 10/2024 Narayan et al.
2024/0400612 A1 12/2024 Narayan et al.
2025/0011395 A1 1/2025 Narayan et al.
2025/0043027 A1 2/2025 Weaver et al.
2025/0059230 A1 2/2025 Upadhyay et al.

FOREIGN PATENT DOCUMENTS

CN 103405756 A 11/2013
CN 103667225 A 3/2014
CN 106190935 A 12/2016
CN 109142728 A 1/2019
CN 109678969 A 4/2019
EP 3620785 A1 3/2020
WO WO-1998/001549 A2 1/1998
WO WO-2002/082066 A1 10/2002
WO WO-2005/044856 A2 5/2005
WO WO-2009/058769 A1 5/2009
WO WO-2010/102241 A1 9/2010
WO WO-2011/150110 A1 12/2011
WO WO-2012/160032 A1 11/2012
WO WO-2013/071396 A1 5/2013
WO WO-2013/096791 A1 6/2013
WO WO-2013/180647 A1 12/2013
WO WO-2015/189832 A1 12/2015
WO WO-2016/009049 A1 1/2016
WO WO-2017/180594 A1 10/2017
WO WO-2019/043067 A1 3/2019
WO WO-2019/224842 A1 11/2019
WO WO-2019/224843 A1 11/2019
WO WO-2021/009669 A2 1/2021
WO WO-2021/038532 A1 3/2021
WO WO-2021/181417 A1 9/2021
WO WO-2021/220251 A1 11/2021
WO WO-2021/220252 A1 11/2021
WO WO-2021/220253 A1 11/2021
WO WO-2021/240458 A2 12/2021
WO WO-2022/195505 A1 9/2022
WO WO-2022/201056 A1 9/2022
WO WO-2023/047368 A1 3/2023
WO WO-2023/053030 A1 4/2023
WO WO-2023/053031 A1 4/2023
WO WO-2023/053032 A1 4/2023
WO WO-2023/057994 A1 4/2023
WO WO-2023/057995 A1 4/2023
WO WO-2023/112000 A2 6/2023
WO WO-2023/180977 A1 9/2023

OTHER PUBLICATIONS

Balbino et al., "The anti-IgE mAb omalizumab induces adverse reactions by engaging Fc receptors", J. Clin. Invest., 2020, 130(3):1330-1335.

Center for Drug Evaluation and Research et al., Product Quality Reviews 2024, FDA, pp. 1-161, https://www.accessdata.fda.gov /drugsatfda_docs/nda/2018/761075Orig 1 s000Chem R. pdf (Year: 2024).

Cohen et al., "Switching Reference Medicines to Biosimilars: A Systematic Literature Review of Clinical Outcomes", Drugs, Mar. 3, 2018, vol. 78, Iss. 4, pp. 463-478. (16 pages).

Friess et al., "Microarray-based identification of differentially expressed growth- and metastasis-associated genes in pancreatic cancer", Cellular and Molecular Life Sciences, vol. 60, Jun. 2003, pp. 1180-1199.

GE Healthcare Life Sciences (2013) Multi modal Chromatography Handbook. GE Healthcare Bio-Sciences AB, Bjorkgatan 30, 751 84 Uppsala, Sweden, 2013, pp. 1-113.

Geng et al., "Inhibition of autoregulated TGFbeta signaling simultaneously enhances proliferation and differentiation of kidney epithelium and promotes repair following renal ischemia", Am. J. Pathol., Dec. 16, 2010, vol. 174, No. 4, pp. 1291-1308.

Goke, et al. (1988) "Identification of Rat Pancreatic Secretory Proteins after Separation by High-Performance Liquid Chromatography," Pancreas 3(2):199-206.

Gu et al. (2019) "Assessment of CE-based baseline disturbances using simulation and targeted experimental evaluation-impact on the purity determination of therapeutic proteins," Analytical and Bioanalytical Chemistry 411:2425-2437.

Guo et al. (2019) "Exploring metabolic biomarkers and regulation pathways of acute pancreatitis using ultra-performance liquid chromatography combined with a mass spectrometry-based metabolomics strategy," RSC Adv 9:12162-12173.

Guttman et al. (2020) "Better Separation Resolution of New Biopharmaceutical Modalities through Fine Tuning of the Temperature with CE-SOS" SCIEX, pp. 1-5.

Herniman et al., "Development of ultrahigh-performance liquid chromatography/mass spectrometry and ultrahigh-performance supercritical fluid chromatography/mass spectrometry assays to determine the concentration of BitrexTM and sodium saccharin in homemade facemask fit testing solutions", Rapid Communications in Mass Spectrometry, vol. 34, Iss. 16, Jun. 3, 2020, pp. 1-6.

International Search Report and Written Opinion for PCT/IB2020/056593 mailed Feb. 8, 2021 (10 pages).

International Search Report and Written Opinion for PCT/IB2020/058080 mailed Feb. 8, 2021 (12 pages).

International Search Report and Written Opinion for PCT/IB2021/053658 mailed Sep. 14, 2021 (15 pages).

International Search Report and Written Opinion for PCT/IB2021/053659 mailed Jul. 22, 2021 (9 pages).

International Search Report and Written Opinion for PCT/IB2021/053660 mailed Aug. 12, 2021 (10 pages).

International Search Report and Written Opinion for PCT/IB2021/054693 mailed Nov. 17, 2021 (7 pages).

International Search Report and Written Opinion for PCT/IB2022/052377 mailed Jun. 30, 2022 (8 pages).

International Search Report and Written Opinion for PCT/IB2022/052651 mailed Jul. 1, 2022 (11 pages).

International Search Report and Written Opinion for PCT/IB2022/059058 mailed Feb. 16, 2023 (8 pages).

International Search Report and Written Opinion for PCT/IB2022/059238 mailed Feb. 24, 2023 (12 pages).

International Search Report and Written Opinion for PCT/IB2022/059239 mailed Feb. 14, 2023 (7 pages).

(56) References Cited

OTHER PUBLICATIONS

International Search Report and Written Opinion for PCT/IB2022/059240 mailed Feb. 23, 2023 (13 pages).
International Search Report and Written Opinion for PCT/IB2022/059648 mailed Feburary 21, 2023 (8 pages).
International Search Report and Written Opinion for PCT/IB2022/059649 mailed Feburary 7, 2023 (8 pages).
International Search Report and Written Opinion for PCT/IB2022/062426 mailed Jun. 6, 2023 (8 pages).
International Search Report and Written Opinion for PCT/IB2023/052862 mailed Jul. 27, 2023 (8 pages).
Jing et al., "Separation of monocloncal antibody charge variants using cation exchange chromatography: Resins and separation conditions optimization", Separation and Purification Technology, vol. 235, Mar. 18, 2020.
Khawli et al., "Charge variants in IgG1: Isolation, characterization, in vitro binding properties and pharmacokinetics in rats", Mabs, Nov.-Dec. 2010, 2(6):613-24. doi: 10.4161/mabs.2.6.13333. (12 pages).
Lacher et al. (2010) "Development, validation, and implementation of capillary gel electrophoresis as a replacement for SDSPAGE for purity analysis of IgG2," mAbs, J. Sep. Sci. 33:218-227.
Lee et al. (2010) "Capillary Electrophoretic Separation of Poly(ethylene glycol)-Modified Granulocyte-Colony Stimulating Factor," Arch Pharm Res 22(3)491-495.
Liu et al. (2005) "Highly efficient approach for characterizing nanometer-sized gold particles by capillary electrophoresis," Analytica Chimica Acta 528: 249-254.
Lou et al., "Liquid-liquid phase separation causes high turbidity and pressure during low pH elution process in Protein A chromatography", Journal of Chromatography, Jan. 28, 2017, vol. 1488, pp. 57-67. (11 pages).
Lui et al. "(2010) Recovery and purification process development for monoclonal antibody production," mAbs 2(5):480-499.
Martias, et al. (2021) "Optimization of Sample Preparation for Metabolomics Exploration of Urine, Feces, Blood and Saliva in Humans Using Combined NMR and UHPLC-HRMS Platforms," Molecules 26(4111) 16 pages.
Molecular Probes, Protein Molecular Weight Standards (P-6649), Jan. 13, 2001, pp. 1-2.
Padfield, et al. (1986) "Separation of Guinea-Pig Pancreatic Juice Proteins by Reversed-Phase High-Performance Liquid Chromatography," Journal of Chroma. 369:133-141.
R&D Systems, Inc., "Recombinant Human CTLA 4 Fc Chimera | Catalog No. 7268-CT". Product datasheet (online). Mar. 6, 2020. (2 pages).
Sanger-van de Griend et al. (2019) "CE-SOS method development, validation, and best practice—An overview," Electrophoresis 40:2361-2374.
Shekhawat et al., "Structural similarity, characterization of Poly Ethylene Glycol linkage and identification of product related variants in biosimilar pegfilgrastim", 1-33, Plos One Web. Mar. 13, 2019. (33 pages).
Singla et al., "Aggregation Kinetics for lgG1-Based Monoclonal Antibody Therapeutics", AAPS J., May 2016, 18(3):689-702. doi: 10.1208/s12248-016-9887-0. (14 pages).
Sobczak et al., "RNA structure analysis assisted by capillary electrophoresis", Nucleic Acids Research, Nov. 15, 2002, vol. 30, No. 22, e124. (8 pages).
Somerville et al. (1999) "Discrimination of granulocyte colony-stimulating factor isoforms by high-performance capillary electrophoresis," Journal of Chromatography B, 732:81-89.
Turner et al., "Development of orthogonoal NISTmAb size heterogeneity control methods", Analytical and Bioanalytical Chemistry, Mar. 2018, vol. 410, No. 8, pp. 2095-2110. (16 pages).
Voitl et al. (2010) "Application of mixed mode resins for the purification of antibodies," Journal of Chromatography A 1217:5753-5760.
Yang et al. (2015) "High resolution separation of recombinant monoclonal antibodies by size-exclusion ultra-high performance liquid chromatography (SE-UHPLC)," Journal of Pharmaceutical and Biomedical Analysis 109:52-61.
Asermely et al., "Identification of a recombinant synaptobrevin-thioredoxin fusion protein by capillary zone electrophoresis using laser-induced fluorescence detection," Journal of Chromatography B 695:67-75 (1997).
Degterev et al. (2011) "Improvement of the Degradation Profiling of Eculizumab and Omalizumab Monoclonal Antibodies by Liquid Chromatography-Mass Spectrometry," Journal of Analytical Chemistry 76(14):1596-1609.
Ichiuhara et al. (2018) "Integrated flow-through purification for therapeutic monoclonal antibodies processing," MABS 10(2):325-334.
Pennington et al. (2016) "Structural basis of omalizumab therapy and omalizumab-mediated IgE exchange," Nature Communications 7:11610:1-12.
Phenomenex: "High Performance Size Exclusion for Biomolecules," Oct. 4, 2010 (Oct. 4, 2010), XP093277516, Retrieved from the Internet: URL:https://phenomenex.blob.core.windows.net/documents/7b9fe422-933e-48df-a189-373e2 ef59503.pdf.
Protein Purification Handbook (2007) GE Healthcare, pp. 1-96 (Year: 2007).
Shen et al., "Formation of an Unprecedented Impurity during CE-SDS Analysis of a Recombinant Protein," Pharm Res 37:228, 12 pages (2020).
Wang et al. Characterization and pre-clinical assessment of a proposed biosimilar to its originator Omalizumab, Eur. J. Pharm Sci 178(1):106292 (2022).
Weisbjerg et al. (2015) "Serial Coupling of Ion-Exchange and Size-Exclusion Chromatography to Determine Aggregation Levels in mAbs in the Presence of a Proteinaceous Excipient, Recombinant Human Serum Albumin," Journal of Pharmaceutical Sciences 104:548-556.
XOLAI R® (omalizumab) product insert https://www.accessdata.fda.gov/drugsatfda_docs/label/2023/103976s5242lbl.pdf 2003.
XOLAIR® (omalizumab) injection for subcutaneous use [package insert]. Accessdata.fda.gov. 2021. https:// www.accessdata.fda.gov/drugsatfda_docs/label/2021/103976s5238lbl.pdf (Year: 2021).

* cited by examiner

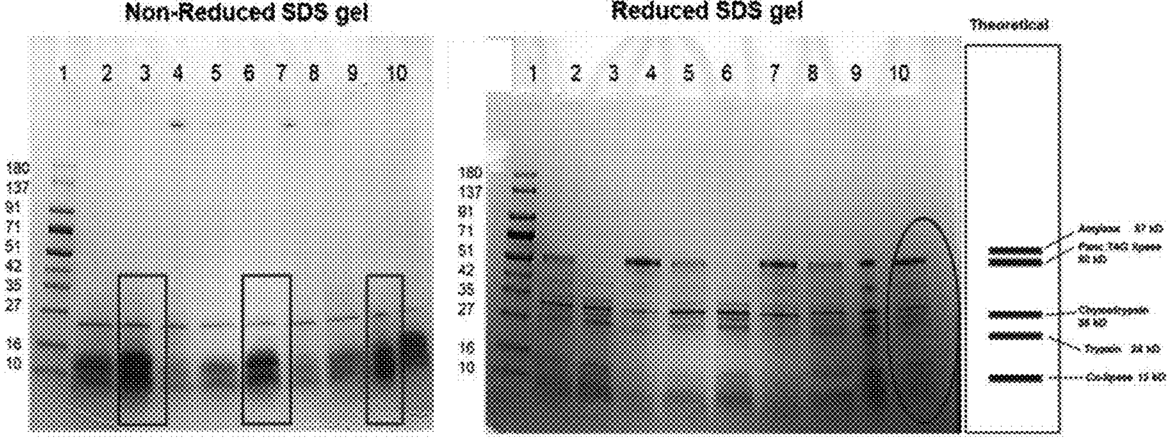
Figure 1: Reduced and Non-reduced SDS PAGE analysis

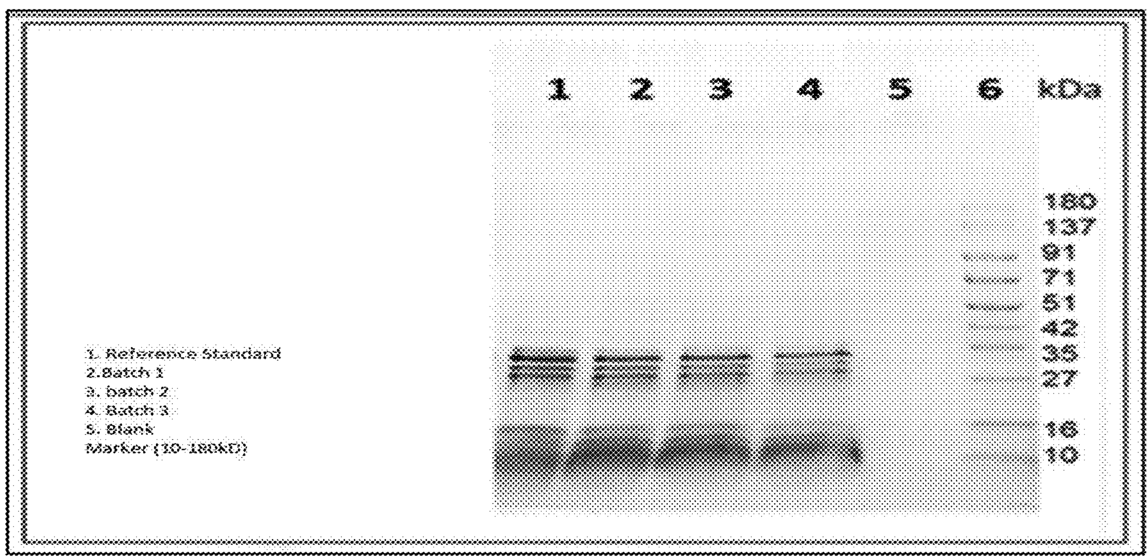
Figure 2. Representative Comparative SDS-PAGE (reduced) profile of Reference standard and samples

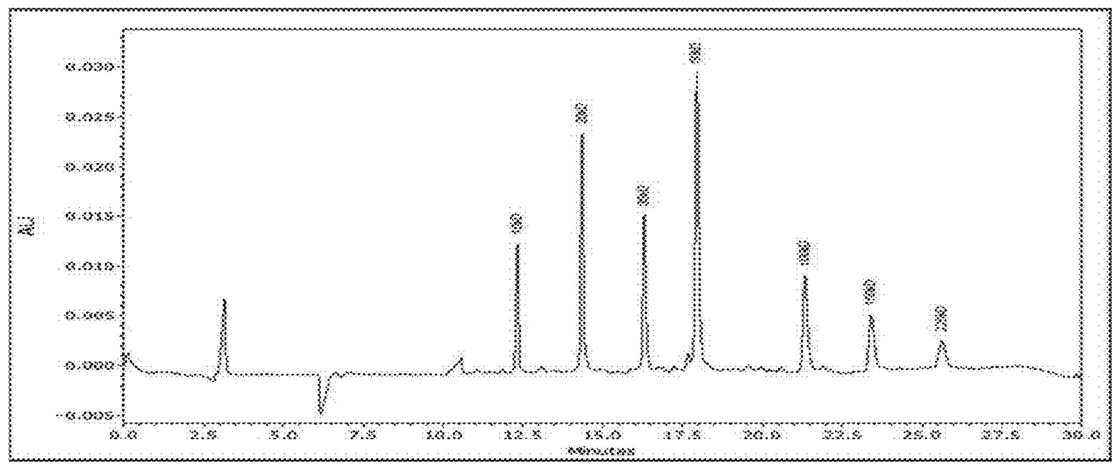
Figure 3: Separation of protein molecular weight size standard

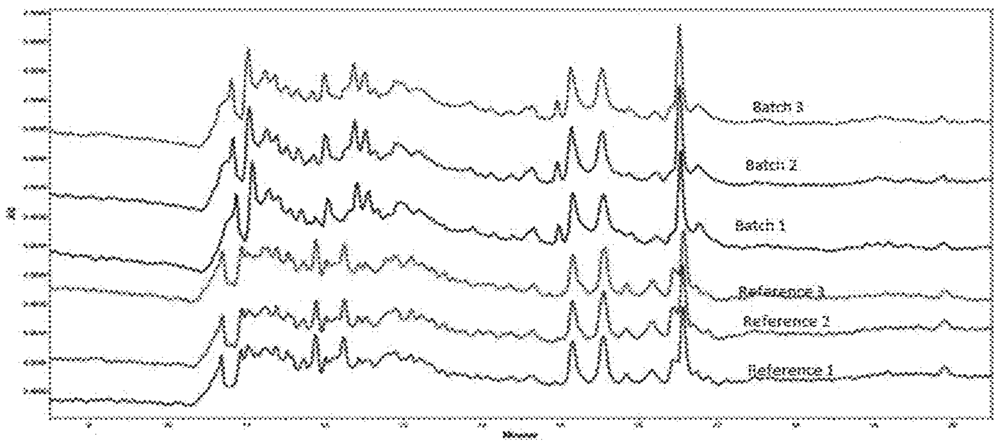
Figure 4: Overlay of Reference standard and Pancrelipase samples

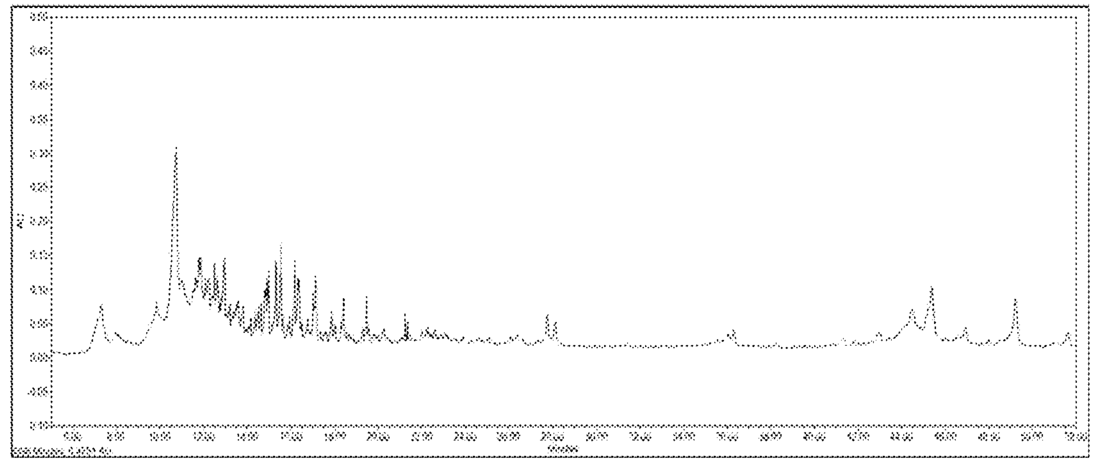
Figure 5. Non-reduced reverse phase chromatographic profile of Reference standard enteric granule extract

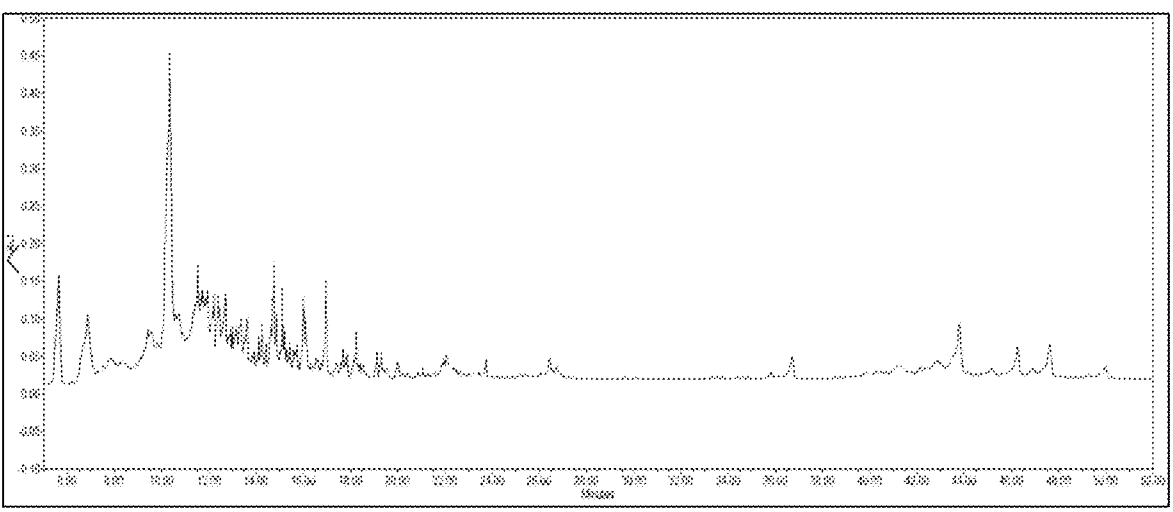
Figure 6. Reduced reverse phase chromatographic profile of Reference standard enteric granule extract

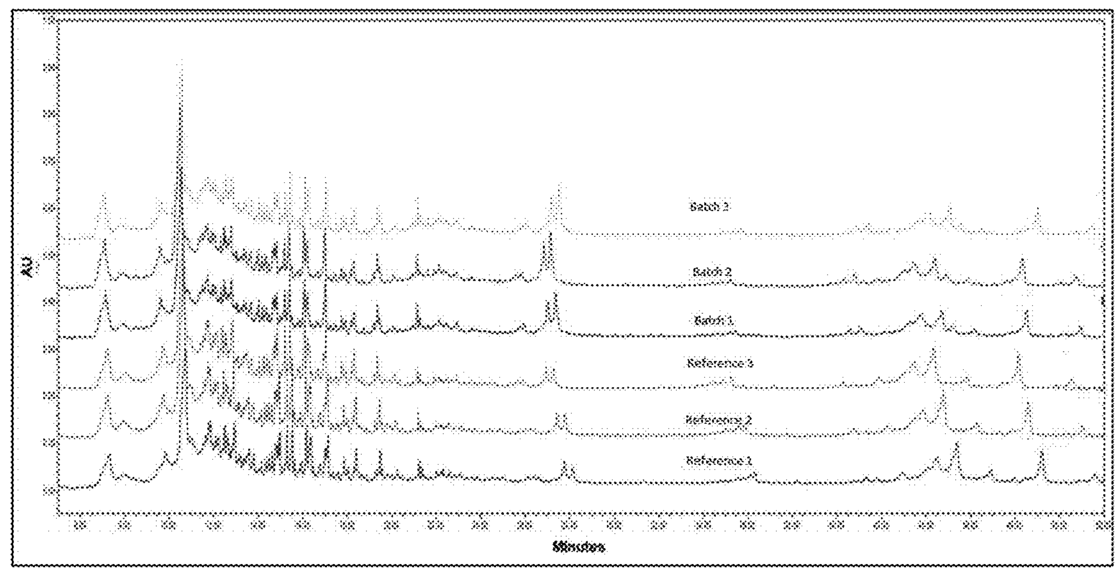
Figure 7. Comparative reverse phase chromatographic (non-reduced) profile of Reference standard and samples

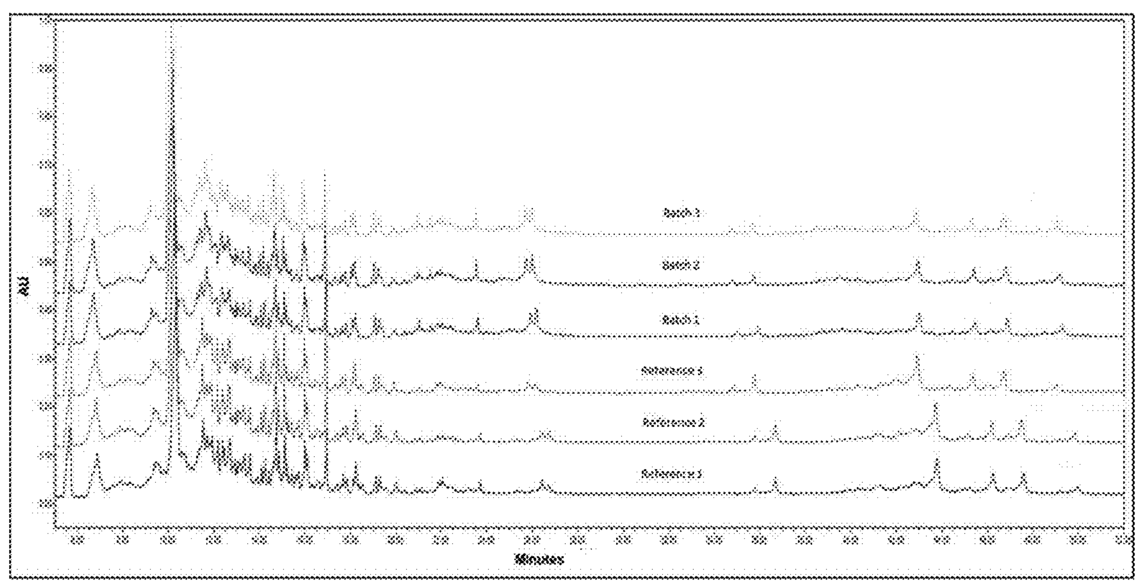
Figure 8. Comparative reverse phase chromatographic (reduced) profile of Reference standard and samples

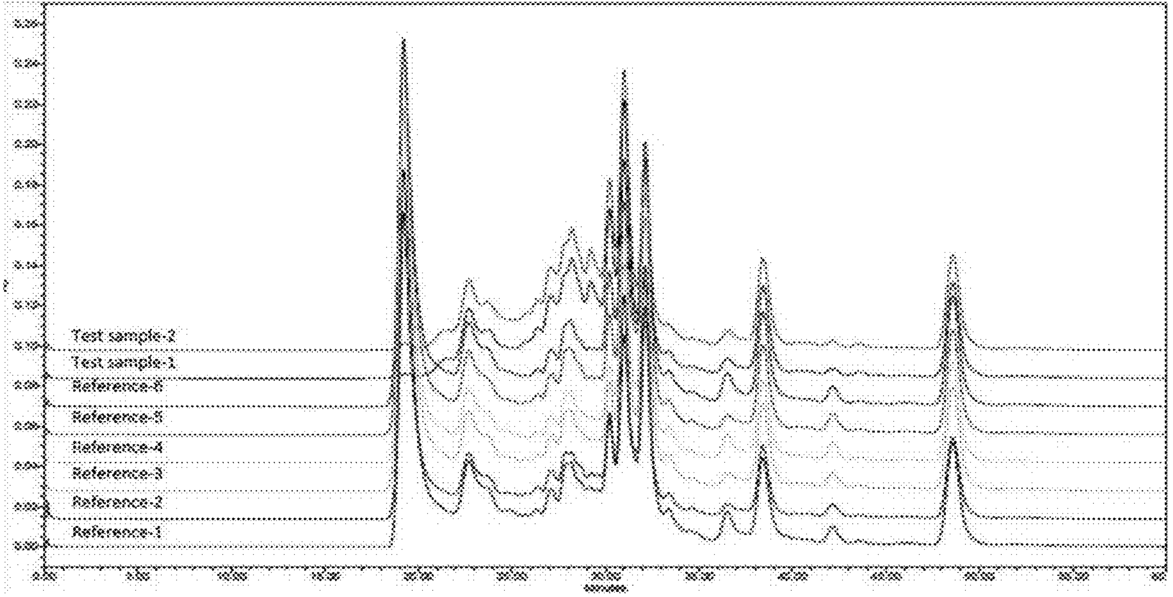
Figure 9: Chromatographic overlay of inhouse and reference product analysed by SE-HPLC under non-reducing condition using 100 mM Citrate Phosphate Buffer with 10 % Acetonitrile as mobile phase.

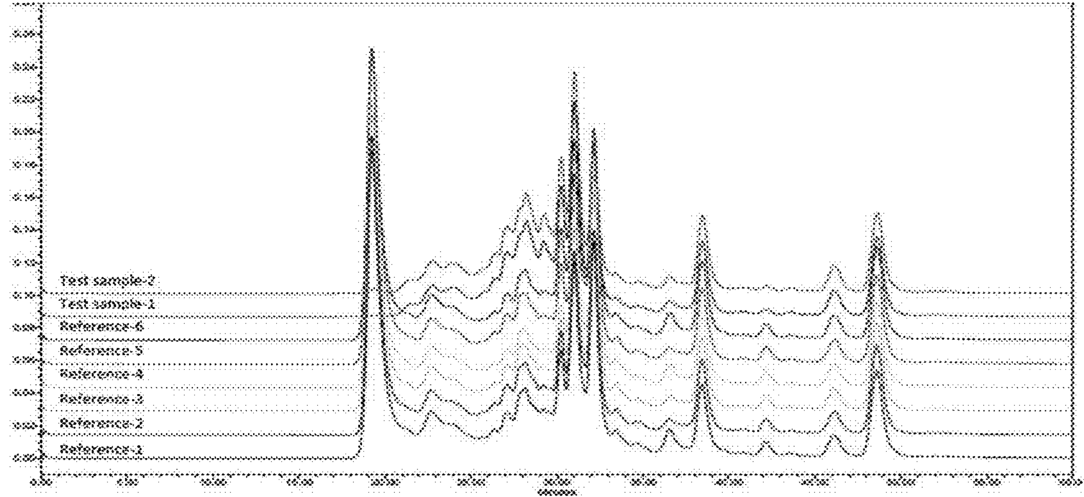
Figure 10: Chromatographic overlay of inhouse and reference product analysed by SE-HPLC under reducing condition using 100 mM Citrate Phosphate Buffer with 10 % Acetonitrile as mobile phase.

EXTRACTION PROCESS OF PANCRELIPASE AND EVALUATION THEREOF

FIELD OF THE INVENTION

The invention relates to a pharmaceutical process used for an extraction of proteins from pancreatic sample and estimation of the extracted proteins. Moreover, the invention provides a use of suitable is selected from citrate-phosphate buffer and bicarbonate buffer capable to extract proteins from pancreatic sample. The invention further provides an analytical method to perform estimation of extracted proteins. This process provides an improved extraction method to quantify protein present in the pancreatic sample.

BACKGROUND OF THE INVENTION

Pancreatic enzymes produced by the body are well known for the integral role they play in the digestion of the foods we eat. Pancreatic juice contains numerous enzymes, including amylase, lipase, protease, cholesterol esterase, and phospholipase, and the proenzymes trypsinogen, chymotrypsinogen, and procarboxypolypeptidase, which are converted in the small intestine to their active forms trypsin, chymotrypsin, and carboxypeptidase, respectively.

As described above, the product is a complex mixture of different proteins present in the pancreatic extracts. This poses a great challenge for organization to characterize all proteins and ensure the product quality. The extraction process requires a selection of suitable buffer in order to extract all proteins from sample. Further the characterization and estimation of pancreatic extracts is very difficult. The extraction process, analytical techniques for estimation of proteins present in pancrelipase plays very important role in developing robust consistent process and pharmaceutically acceptable biosimilar product.

Thus, the present invention provides a pharmaceutical process used for extraction of proteins from pancreatic sample and estimation of the extracted proteins. The invention provides a use of buffer capable to extract proteins from pancreatic sample in desired amount and reduced the loss of protein of interest during extraction and thereby the present method is very economic. The invention further provides an analytical method to perform estimation of extracted proteins. This process provides an improved extraction method to quantify protein present in pancreatic sample.

SUMMARY OF THE INVENTION

In an embodiment the invention provides a process for an extraction of pancreatic protein from pancreatic protein sample comprises:

a. treating the pancreatic protein sample with suitable buffer selected from citrate-phosphate and bicarbonate buffer at suitable pH;
b. dissolving the pancreatic protein sample in the buffer;
c. collecting the extracted pancreatic protein.

In an embodiment the invention provides improved extraction process for the extraction of pancreatic protein with citrate phosphate buffer in comparison to the extraction process performed without using citrate-phosphate buffer.

In another embodiment the invention provides an improved extraction process for the extraction of pancreatic protein with bicarbonate buffer in comparison to the extraction process performed without using bicarbonate buffer.

In certain embodiment the invention provides a buffer concentration is selected from about 10 mM to about 200 mM.

In certain embodiment the pH of citrate buffer is selected from about 6.0, about 6.1, about 6.2, about 6.3, about 6.4 and about 6.5.

In certain embodiment the pH of bicarbonate buffer is selected from and about 9.5, about 9.6, about 9.7, about 9.8 and about 10.

In an embodiment, the estimation of protein performed by using BCA Kit.

In an embodiment, the process provides pancreatic protein yield at least about 80% to 100% from pancreatic protein sample.

In an embodiment the invention performs the estimation of extracted protein by using SDS-PAGE, CE-SDS, SE-HPLC and RP-HPLC method.

In an embodiment the invention provides a pharmaceutically acceptable pancreatic protein mixture comprising one or more enzymes selected from amylase, lipase and protease.

In an embodiment the quantification of pancreatic protein is performed by using method selected from SDS-PAGE, CE-SDS, SE-HPLC and RP-HPLC method.

This process provides an improved extraction method to quantify protein present in pancreatic sample by using suitable buffer selected from citrate-phosphate buffer and bicarbonate buffer.

BRIEF DESCRIPTION OF FIGURES

FIG. 1: Depicts the reduced and non-reduced SDS PAGE analysis

1. Marker (10-180 kDa)
2. USP lipase-sodium phosphate buffer
3. USP lipase-citrate phosphate buffer
4. USP lipase-bicarbonate buffer
5. USP Protease amylase std.—sodium phosphate buffer
6. USP Protease amylase std.—citrate phosphate buffer
7. USP Protease amylase std.—bicarbonate buffer
8. Reference standard extract—sodium phosphate buffer
9. Reference standard extract—citrate phosphate buffer
10. Reference standard extract—bicarbonate buffer FIG. 2. Representative Comparative SDS-PAGE (reduced) profile of Reference standard and samples.

FIG. 3: Separation of protein molecular weight size standard.

Based on molecular weight size standard shown in FIG. 3, apparent molecular weight of the pancreatic protein extracted with citrate phosphate buffer is identified.

FIG. 4: Overlay of Reference standard and Pancreatic samples.

FIG. 5. Non-reduced reverse phase chromatographic (RPC) profile of Reference standard enteric granule extract.

FIG. 6. Reduced reverse phase chromatographic profile of Reference standard enteric granule extract.

FIG. 7. Comparative reverse phase chromatographic (non-reduced) profile of Reference standard and samples.

FIG. 8. Comparative reverse phase chromatographic (reduced) profile of Reference standard and samples.

FIG. 9: Chromatographic overlay of inhouse and reference product analysed by SE-HPLC under non-reducing condition using 100 mM Citrate Phosphate Buffer with 10% Acetonitrile as mobile phase.

It is evident from FIG. 9 that the pancreatic protein extracted with citrate phosphate buffer shows the batch to batch consistency.

FIG. 10: Chromatographic overlay of inhouse and reference product analysed by SE-HPLC under reducing condition using 100 mM Citrate Phosphate Buffer with 10% Acetonitrile as mobile phase.

It is evident from FIG. 10 that the pancreatic protein extracted with citrate phosphate buffer shows the batch to batch consistency.

Comparative size-based qualitative profile of the constituent proteins obtained through reduced and non-reduced CE-SDS need to be represented in the form of an overlay (FIGS. 9 and 10). Similarity between protein profiles observed between Reference standard and the samples needs to be inferred.

DETAILED DESCRIPTION OF THE EMBODIMENTS

Definitions

Unless the context clearly requires otherwise, throughout the invention, the words "comprise", "comprising", and the like are to be construed in an inclusive sense as opposed to an exclusive or exhaustive sense; that is to say, in the sense of "including, but not limited to".

The term "about" as used herein is intended to refer to ranges of approximately 10 to 20% greater than or less than the referenced value. In certain circumstances, one skill in the art will recognize that, due to the nature of the referenced value, the term about can mean more or less than a 10% to 20% deviation from that value.

The term "a suitable buffer" refers to citrate phosphate buffer, and bicarbonate buffer.

The term "Reference standard" refers pancrelipase product which are approved by regulatory agencies FDA and EMA. In certain embodiment the reference standard is selected from creon, Pancreaze, Pancrelipase, Pangestyne EC, Pangestyme C, Panocaps, Pertzye, Ultracaps, Ultresa, Viokace, Zenpep.

In an embodiment the reference standard is Creon.

The term "Pancrelipase samples" or "pancreatic sample" or "pancreatic protein sample" refers to pancreatic digestive enzymes formulated in any pharmaceutical composition. In an embodiment the pancrelipase sample is selected from granules, tablet, capsules and powder. The "Pancrelipase samples" or "pancreatic sample" or "pancreatic protein sample" comprises at one enzyme selected from lipase, protease, amylase and combination thereof. In embodiment the "Pancrelipase samples" or "pancreatic sample" or "pancreatic protein sample" obtained from crude, partially purified, substantially purified and microbially synthesize.

In an embodiment, the pancreatic protein sample comprises enzymes selected from Triacylglycerol lipase, Colipase, CEL lipase, Phospholipase A2, Trypsin, Chymotrypsin, Elastase, Carboxypeptidase A1, Carboxypeptidase B, Kallikrien glandular, and Alpha amylase are the prominent functionally important enzymes.

The term "substantially dissolves" refers to completely dissolving the pancreatic protein sample in buffer. In one embodiment substantially dissolves means pancreatic protein sample dissolves selected from about 99%, about 98%, about 99%, and 100% in buffer. Further dissolution of pancreatic protein in buffer is an important parameter to avoid the loss of protein of interest. Further provides suitable solution of pancreatic protein for analysis.

The term "Pancreatic protein" refers to pancrelipase sample which is substantially dissolve in citrate phosphate buffer or bicarbonate buffer thereby desired pancreatic protein is obtained through extraction which comprises at least one enzyme is selected from protease, lipase and amylase and combination thereof. In an embodiment, pancreatic protein substantially contains desired digestive enzymes in a solution suitable for performing further analysis using SDS-PAGE, CE-SDS, SE-HPLC and RP-HPLC method.

In one embodiment, the estimated yield of pancreatic protein depends on type of pancreatic protein sample used.

In one embodiment, the method provides the yield of pancreatic protein more than about 80%. For extraction for an example if granules contain 5 mg/ml, the present method at least extract more than about 80%, more than about 90% and most probably 100% of it.

In one embodiment, the method provides the yield of pancreatic protein is selected from about 80%, about 81%, about 82%, about 83%, about 84%, about 85%, about 86%, about 87%, about 88%, about 89%, about 90%, about 91%, about 92%, about 93%, about 94%, about 95%, about 99%, and about 100%.

The present invention provides the improved extraction process for extraction of proteins from pancreatic protein sample and estimation of the extracted proteins, wherein the extraction and the estimation of protein from pancreatic protein sample is performed with suitable buffer.

In one embodiment, an invention provides improved extraction process for an extraction of pancreatic protein from pancreatic protein sample comprises:

a. treating the pancreatic protein sample with suitable buffer selected from citrate-phosphate and bicarbonate buffer at suitable pH;
b. dissolving the pancreatic protein sample in the buffer;
c. collecting the extracted pancreatic protein.

In an embodiment the invention provides an improved extraction process for the extraction of pancreatic protein with citrate phosphate buffer in comparison to the extraction process performed without using citrate-phosphate buffer.

In another embodiment the invention provides an improved extraction process for the extraction of pancreatic protein with bicarbonate buffer in comparison to the extraction process performed without using bicarbonate buffer.

In certain embodiment the invention provides a buffer concentration is selected from about 10 mM to about 200 mM.

In certain embodiment the pH of citrate buffer is selected from about 6.0, about 6.1, about 6.2, about 6.3, about 6.4 and about 6.5.

In certain embodiment the pH of bicarbonate buffer is selected from and about 9.5, about 9.6, about 9.7, about 9.8 and about 10.

In an embodiment the invention performs the estimation of extracted protein by using SDS-PAGE, CE-SDS and RP-HPLC method.

In an embodiment the invention provides a pharmaceutically acceptable pancreatic protein mixture comprising one or more enzymes selected from amylase, lipase and protease.

In an embodiment, the extraction of protein is performed by using citrate phosphate buffer.

In preferable embodiment, the buffers are used for evaluating the most appropriate buffer for extraction of proteins from pancreatic protein sample comprises citrate phosphate buffer.

In an embodiment the invention provides improved extraction process for an extraction of pancreatic protein from pancreatic protein sample comprises:

a. treating the pancreatic protein sample with suitable buffer selected from citrate-phosphate at suitable pH;

b. dissolving the pancreatic protein sample in the buffer;

c. collecting the extracted pancreatic protein;

wherein the extraction of pancreatic protein with citrate phosphate buffer is improved in comparison to the extraction process performed without using citrate-phosphate buffer.

In an embodiment, the pH of citrate phosphate buffer is maintained from and about 6.0 to about 6.5.

In an embodiment, the pH of citrate phosphate buffer is maintained from and about 6.0, about 6.1, about 6.2, about 6.3, about 6.4 and about 6.5.

In an embodiment, the pH of citrate phosphate buffer is maintained from and about 6.0, and about 6.5.

In an embodiment, the concentration of citrate-phosphate buffer is selected from about 10 mM to about 200 mM.

In one embodiment, the concentration of citrate-phosphate buffer used from about 10 mM, about 15 mM, about 20 mM, about 25, about 30 mM, about 35, about 40 mM, about 45, about 50 mM, about 55, about 60 mM, about 65, about 70 mM, about 75, about 80 mM, about 85, about 90 mM, about 95, about 100 mM, about 105 mM, about 110 mM, about 115 mM, about 120 mM, about 125 mM, about 130 mM, about 135 mM, about 140 mM, about 145 mM, about 150 mM, about 155 mM, about 160 mM, about 165 mM, about 170 mM, about 175 mM, about 180 mM, about 185 mM, about 190 mM, about 195 mM, about 200 mM.

In an embodiment, the concentration of citrate-phosphate buffer is about 100 mM.

In an embodiment, the extraction of protein is performed by using bicarbonate buffer.

In an embodiment the invention provides improved extraction process for an extraction of pancreatic protein from pancreatic protein sample comprises:

a. treating the pancreatic protein sample with bicarbonate buffer at suitable pH;

b. dissolving the pancreatic protein sample in the bicarbonate buffer;

c. collecting the extracted pancreatic protein;

wherein the extraction of pancreatic protein with bicarbonate buffer is improved in comparison to the extraction process performed without using bicarbonate buffer.

In another embodiment, the pH of bicarbonate buffer is maintained from and about 9.5 to about 10.

In another embodiment, the pH of bicarbonate buffer is maintained from and about 9.5, about 9.6, about 9.7, about 9.8 and about 10.

In another embodiment, the pH of bicarbonate buffer is maintained from and about 9.5, and about 10.

In an embodiment, the concentration of bicarbonate buffer is selected from about 10 mM to about 200 mM.

In one embodiment, the concentration of bicarbonate buffer used from about 10 mM, about 15 mM, about 20 mM, about 25, about 30 mM, about 35, about 40 mM, about 45, about 50 mM, about 55, about 60 mM, about 65, about 70 mM, about 75, about 80 mM, about 85, about 90 mM, about 95, about 100 mM, about 105 mM, about 110 mM, about 115 mM, about 120 mM, about 125 mM, about 130 mM, about 135 mM, about 140 mM, about 145 mM, about 150 mM, about 155 mM, about 160 mM, about 165 mM, about 170 mM, about 175 mM, about 180 mM, about 185 mM, about 190 mM, about 195 mM, about 200 mM.

In an embodiment, the concentration of bicarbonate buffer is 100 mM.

In an embodiment, the pancreatic sample or pancreatic protein is substantially dissolved by using suitable method known in the art e.g., shaking, stirring etc. In an embodiment one skilled person in art can use other method for dissolving the treated pancreatic sample based on the common general knowledge.

In an embodiment, the treated pancreatic sample is stirred for suitable time selected from about 20 to about 30 minutes.

In one aspect of such embodiment the pancreatic sample is stirred for suitable time selected from about 20 minutes, about 21 minutes, about 22 minutes, about 23 minutes, about 24 minutes, about 25 minutes, about 26 minutes, about 27 minutes, about 28 minutes, about 29 minutes and about 30 minutes.

In an embodiment, the treated pancreatic sample is stirred at suitable rpm selected from about 200 rpm to about 300 rpm.

In one aspect of such embodiment pancreatic sample is stirred at suitable rpm selected from 200 rpm, 210 rpm, 220 rpm, 230 rpm, 240 rpm, 250 rpm, 260 rpm, 270 rpm, 280 rpm, 290 rpm, and 300 rpm.

In an embodiment the quantification of pancreatic protein is performed by using method selected from SDS-PAGE, CE-SDS, SE-HPLC and RP-HPLC method.

In an embodiment, the estimation of protein performed by using BCA, SDS-PAGE, CE-SDS, SE-HPLC and RP-HPLC method.

In an embodiment, the invention provides a process of estimation of extracted pancreatic proteins by using BCA. In an embodiment one skilled person in art can use other kit or extraction process.

In an embodiment, the invention provides a process of estimation of extracted pancreatic proteins by using CE-SDS.

In another embodiment, the invention provides a process of estimation of extracted pancreatic proteins by using RP-HPLC.

In another embodiment, the invention provides a process of estimation of extracted pancreatic proteins by using SDS-PAGE.

In another embodiment, the invention provides an extraction of proteins by using citrate phosphate buffer and further perform the process of estimation of extracted proteins by using CE-SDS.

In another embodiment, the invention provides an extraction of proteins by using citrate phosphate buffer and further perform the process of estimation of extracted proteins by using SE-HPLC.

In another embodiment, the invention provides a process of estimation of extracted proteins by using SE-HPLC.

In another embodiment, the invention provides an extraction of proteins by using citrate phosphate buffer and further perform the process of estimation of extracted proteins by using RP-HPLC.

In another embodiment, the invention provides an extraction of proteins by using citrate phosphate buffer and further perform the process of estimation of extracted proteins by using SDS-PAGE.

In one embodiment, molecular weight of enzyme proteins is calculated based on SDS-PAGE analysis.

In another embodiment, the invention provides an extraction of proteins by using bicarbonate buffer and further perform the process of estimation of extracted proteins by using CE-SDS.

In another embodiment, the invention provides an extraction of proteins by using bicarbonate buffer and further perform the process of estimation of extracted proteins by using RP-HPLC.

In another embodiment, the invention provides an extraction of proteins by using bicarbonate buffer and further perform the process of estimation of extracted proteins by using SE-HPLC.

In another embodiment, the invention provides an extraction of proteins by using bicarbonate buffer and process of estimation of extracted proteins by using SDS-PAGE. In an embodiment, in protein extraction method for short term storage before analysis place the samples at about 2° C. to about 8° C. and for long term usage these sample can be stored in a −80° C. refrigerator.

In an embodiment the invention provides a pharmaceutically acceptable pancreatic protein mixture comprising one or more enzymes selected from amylase, lipase and protease.

EXAMPLES

Example 1: Process for Extraction and Estimation of Proteins From Pancrelipase Granules Materials and reagents used for the process of the extraction and estimation are: Water, Citric Acid, $Na_2HPO_4$, Micro Filter (0.2 μm), Microfuge tubes, Weighing Boat, Syringe, BCA Kit, 10×PBS Buffer, 15 mL centrifuge tubes, and 50 mL centrifuge tubes.

Evaluation of buffers: Several buffers were used for evaluating the most appropriate buffer for extraction of proteins from Pancrelipase granules given in Table 1 below:

| Buffer | pH | Conditions | Observations |
|---|---|---|---|
| Water | Milli Q | Pancrelipase granules subjected to 100 rpm in the respective buffers for 30 min | insoluble |
| Chilled water | Milli Q | | insoluble |
| Citrate buffer | 3.0 | | insoluble |
| Citrate phosphate buffer (Mc Ilvain's buffer) | 6.0 | | soluble |
| Citrate phosphate buffer (Mc Ilvain's buffer) | 6.5 | | soluble |
| Sodium Phosphate buffer | 6.8 | | soluble with slight turbidity |
| Sodium Phosphate buffer | 7.0 | | soluble with slight turbidity |
| Sodium Phosphate buffer | 7.5 | | soluble with slight turbidity |
| Bicarbonate buffer | 9.5 | | soluble |
| Bicarbonate buffer | 10.0 | | soluble |
| Crushed granules | 3.0, 6.0, 9.0 | Crushed granules solubilized in water, phosphate, citrate, and bicarbonate buffer | Except for bicarbonate buffer all the buffers led to extremely turbid solution |

Amongst the several buffers used for evaluating the most appropriate buffer for extraction of proteins from pancrelipase granules, it was observed that the granules dissolved better in citrate-phosphate buffer, and bicarbonate buffer. These were further observed for release of proteins and assessment through SDS-PAGE and CE-SDS. Also analysed with RP-HPLC method wherein, SDS-PAGE and CE-SDS were used for separation of protein species based on their molecular sizes whereas RP-HPLC was used for separation of proteins based on their hydrophobicity. The released proteins were estimated by uv spectrophotometer at 280 nm.

Preparation of Extraction Buffer, e.g., 100 Mm Citrate Phosphate Buffer: For the preparation of 100 mM of Citrate Phosphate Buffer, Na2HPO4 of 7.098 g was weighed and transferred into a glass beaker containing 300 mL of purified water. This was stirred well on a magnetic stirrer and allowed to dissolve properly. 100 mM citric acid solution was used to adjust the pH to 6.20. The volume was made up to 500 mL with purified water and the solution filtered with 0.2μ filter using vacuum pump. 100 mM Citric Acid Solution was prepared by dissolving 3.84 g of citric acid in 150 mL of purified water. This was mixed well, and volume made up to 200 mL with purified water.

Process of Protein Extraction: For the protein extraction method, we accurately weighed 125.0 mg of pancrelipase granules each of reference and samples, respectively and the granules transferred to a 100 mL volumetric flask. 25 mL of Citrate phosphate buffer was added to the volumetric flask, and stoppered. This was clamped on a wrist shaker equipment and stirred at 300 RPM for at least 30 minutes. The solution was checked for dissolution of granules have dissolved properly and the solution appears slight cream pale colour. The citrate phosphate buffer solution (1 ml) was syringe filtered with a 0.2 μm microfilter unit as equilibration step before proceeding for filtration of sample solution. The reference/sample solution was taken in this syringe and the filtrate was collected extracted reference/sample solution. This protein concentration of the filtered sample or extract was estimated by using BCA kit method. For short term storage before analysis place the samples at 2-8° C. and for long term usage these sample can be stored in a −80° C. refrigerator. Avoid multiple freeze thaw cycles by preparing aliquots after extraction and freezing them.

Process of Protein Estimation:

a. Preparation of BCA working reagent: For the preparation of BCA reagent, 50 mL of reagent A (BCA solution) was taken and added 1 mL of reagent B [copper (II) sulphate pentahydrate 4% solution] and mixed well in a 50 mL centrifuge tube.

b. Preparation of 1×PBS buffer: buffer 2 mL of (10×PBS) was taken then 18 mL of purified water was added to it, mixed it well.

c. Preparation of BSA standards for the standard plot given in Table 2 below:

| Solution Concentration (mg/mL) | BSA Standard (1 mg/mL) | 1X PBS |
|---|---|---|
| 0.2 | 40 μL | 100 μL |
| 0.4 | 80 μL | 120 μL |
| 0.6 | 120 μL | 80 μL |
| 0.8 | 160 μL | 40 μL |
| 1.0 | 200 μL | -NA- |

d. Preparation of reaction blank solution: 100 μL of 1×PBS was taken and 2 mL of BCA working reagent was added to it and mixed it well.

e. Preparation of reference/samples for protein estimation: 50 μL of protein samples were taken and added 150 μL of diluent (1×PBS) to it and mixed it well. This dilution is in a ratio of 1:3. The volumes can be varied keeping the ratio intact. Taken 100 μL of above solution and added 2 mL of BCA working reagent to it and mixed well. Incubated all preparations which is BSA linearity standard solutions, Blank solution, reference, and samples, at room temperature for 2.5-3 h. The incubation can be extended up to 4 h but not less than 2.5 h. After the incubation time, measured the absorbance measurement of all the above solutions at 562 nm wavelength in a UV spectrophotometer.

f. Determination of protein concentration: Sample dilution factor (for 1:3 ratio the dilution factor would be 4) was applied to obtain the final reportable protein concentration in mg/mL. The standard curve between absorbance at 562 nm Vs. Concentration (mg/mL) was determined for linearity (R2), slope (m) and intercept (c) value, for the BSA standards. Based on the OD at 562 nm values obtained for the reference/samples, back calculated concentration was taken the values of the standard curve into consideration as follows. The OD at 562 nm for a sample was found to be 0.441, and the concentration was calculated based on the formula:

$$y=mx+c$$

$$x=(y-c)/m$$

$$=(0.441-0.0373)/0.7695$$

$$=0.5246$$

$$x=0.5246*\text{Dilution Factor}$$

$$=0.5246*4$$

=2.1 mg/Ml

For Slope (m): 0.7695

For Intercept (c): 0.0373

Dilution factor: 4

Result: Among all the buffered used the citrate-phosphate buffer and the bicarbonate buffer are best for the extrations.

It is evident from FIG. 1 that both reducing and non-reducing SDS-PAGE that the intensity of protein bands is comparatively higher in pancreatic mixture of USP lipase, protease and amylase standard extracted in citrate-phosphate buffer.

Intensity of bands in a pancreatic mixture of reference standard extracted with citrate-phosphate buffer and bicarbonate buffer was higher in comparison to sodium-phosphate buffer indicating that both extraction buffers can be used.

Example 2: Estimation of Protein by Using SDS-PAGE Method Comprises Following Step Materials and Reagent used for the SDS-PAGE method are: Purified Water, 10× Tris/Glycine buffer, Pre-cast gel (4-20%), Sample Reducing agent (10×), NuPAGE, LDS sample buffer, Protein ladder-4 color, 10-180 kDa, Citric Acid, Na2HPO4, Staining solution, Methanol, and Glacial acetic acid.

a. Preparation of Diluent buffer e.g., 100 Mm Citrate Phosphate Buffer preparation process is mentioned above.

b. For the Preparation of running buffer e.g., 1× Tris Glycine buffer—For the preparation of running buffer added 100 mL of 10× Tris Glycine buffer and made up the volume to 1000 mL with purified water then mixed it well and transferred it in a bottle.

c. Destaining solution: 100 mL of purified water was taken and added 80 mL of methanol, mixed it well. Added 20 mL of Glacial acetic acid to this solution and mixed well in a glass bottle.

d. Preparation of Pancrelipase test sample: For the preparation of pancrelipase test sample we referred method for protein extraction and estimation we mentioned above. Protein concentration value for pancrelipase extract is determined by BCA kit method. Considered this value for further dilution of non-reducing and reducing samples.

e. Preparation of Reducing Sample: Diluted the sample to 1.0 mg/mL with citrate phosphate buffer for a total sample volume of 100 μL. 18 μL of this sample was taken and added 6 μL of sample reducing agent and mixed it well, incubated this sample at 90° C. for 4 min. Allowed it to cool down to room temperature and give a short spin to the sample tubes. This sample is loaded based in the well based on the sample concentration to achieve final on-gel protein load of 10-15 μg. For samples of 1 mg/mL added about 10 μL and for samples below 1 mg/mL add volume such as to achieve final on-gel protein load of 10-15 μg.

Details of SDS-PAGE Given in Table 3 Below:

| | |
|---|---|
| Gel | 4-20% precast gel |
| Running buffer | 1X Tris Glycine SDS buffer |
| Voltage | 140 V |
| Run time | About 1 h or till loading dye front reaches the line marked on the precast gel cassette |

After completion of the run the pre-cast gel cassette is broken on the arrows indicated and rinsed in purified water carefully. Transferred the gel in a box containing staining solution. After sufficient staining of the gel (about 20 min), staining solution is removed. The gel is then rinsed with purified water shortly before transferring it into destaining solution. Allowed to destain till the background coloration is removed and the bands appear clearly. Transferred the gel in purified water and keep it overnight, if required, before taking gel picture.

The extracted protein was evaluated for the citrate phosphate, sodium phosphate buffer, and bicarbonate buffer by SDS-PAGE (4-20%). This was also compared to the USP standards in the same buffers to have a size-based comparison. It was observed to give a better protein yield in citrate phosphate buffer, in the size range corresponding to the expected theoretical protein sizes (FIG. 1).

It is evident from FIG. 2 that the pancreatic protein extracted with citrate phosphate buffer shows the batch to batch consistency.

Example 3: Estimation of Protein by Using CE-SDS Method

CE-SDS was utilized for understanding the size-based protein species and was further used for comparison of the reference and in-house protein product. CE-SDS assist in demonstrating similarity and differences based on size variants.

Materials and reagents used for CE-SDS method are: IgG Purity/Heterogeniety Kit, SDS-MW Gel Buffer Multipack, MW Size Standard, 10 kDa standard, Pre-Assembled Capillary Cartridge, Vials, Caps, Micro Vials, Iodoacetamide, Milli Q Water, and Betamercapto ethanol.

The Procedure for estimation of protein by using CE-SDS method:

Preparation of the Alkylation reagent (250 mM IAM solution): Weighed 46 mg of iodoacetamide (IAM). Transferred IAM to a centrifuge tube. Added 1.0 mL of milli Q water to the centrifuge tube. Cap the vial tightly, mixed thoroughly until dissolved using vortex, and then stored in the dark place. The IAM solution is stable for approximately 24 hours at room temperature. This solution should be prepared fresh.

1. Preparation of SDS MW size standard: Pipptte 10 μL of Size standard into a centrifuge vial. Added 85 μL of sample buffer into the centrifuge vial. Added 5 μL of 2-mercaptoethanol. Cap the vial tightly, seal with Parafilm, and mixed thoroughly. Heated mixture in a water bath at 100° C. for three minutes. Placed the vial in a room-temperature to cool for five minutes before injection. Transferred 90 μL of the sample into a micro vial.

2. Preparation of blank: Pipptte 45 μL of buffer into a centrifuge vial. Added 55 μL of sample buffer into the centrifuge vial. Added 5 μL of 250 mM IAM solution. Cap the vial tightly, seal with Parafilm, and mixed thoroughly. Heated mixture in a water bath at 70° C. for three minutes. Placed the vial in a room-temperature to cool for five minutes before injection. Transferred 90 μL of the sample into a micro vial.

3. Preparation of sample: Diluted the sample to get the any concentration in the range of 0.5 mg/mL to 1.5 mg/mL using milli Q water. Samples should preferably be diluted to 1.0 mg/mL or to any fixed concentration in above range based on objective of study. Final salt concentration should preferably be less than 50 mM. Samples above 80 mM should be diluted to final salt concentration less than 80 mM and concentration not less than 0.5 mg/mL.

Pipptte 45 μL of buffer into a centrifuge vial. Added 55 μL of sample buffer into the centrifuge vial. Added 5 μL of 250 mM IAM solution. Cap the vial tightly, seal with parafilm, and mixed thoroughly. Heated mixture in a water bath at 70° C. for three minutes. Placed the vial in a room-temperature to cool for five minutes before injection. Transferred 90 μL of the sample into a micro vial.

4. Preparation of Buffer trays (Inlet and outlet):

i. Buffer Inlet Tray: Prepared the buffer inlet tray as per the schematic shown in the Table 4 below and loaded on the left side of the instrument.

TABLE 4

Inlet buffer tray configuration

| No. | A | B | C | D | E | F |
|---|---|---|---|---|---|---|
| 6 | $H_2O$ (Cycle 24-35) | $H_2O$ (Cycle 24-35) | | | | |
| 5 | $H_2O$ (Cycle 12-23) | $H_2O$ (Cycle 12-23) | | | | |
| 4 | $H_2O$ (Cycle 1-11) | $H_2O$ (Cycle 1-11) | | | | |
| 3 | $H_2O$ (Cycle 24-35) | Gel-R (Cycle 24-35) | Gel-S (Cycle 24-35) | NaOH (Cycle 24-35) | HCl (Cycle 24-35) | $H_2O$ (Cycle 24-35) |
| 2 | $H_2O$ (Cycle 12-23) | Gel-R (Cycle 12-23) | Gel-S (Cycle 12-23) | NaOH (Cycle 12-23) | HCl (Cycle 12-23) | $H_2O$ (Cycle 12-23) |
| 1 | $H_2O$ (Cycle 1-11) | Gel-R (Cycle 1-11) | Gel-S (Cycle 1-11) | NaOH (Cycle 1-11) | HCl (Cycle 1-11) | $H_2O$ (Cycle 1-11) |

Al to A6—Water, use in dip step to clean capillary tip, 1.5 mL

B4 to B6—Water, use in dip step to clean capillary tip, 1.5 mL

B1 to B3—Gel-R (SDS-MW gel buffer), use to rinse/fill capillary prior to each cycle, 1.2 mL C1 to C3—Gel-S (SDS-MW gel buffer), use for separation, 1.1 mL Dl to D3—0.1N NaOH, use to precondition capillary, 1.5 mL E1 to E3—0.1N HCl, use to precondition capillary, 1.5 mL Fl to F3—Water, use to precondition capillary, 1.5 mL ii. Buffer Outlet Tray: Prepared the buffer outlet tray as per the schematic shown in the Table 5 below and loaded on the right side of the instrument.

TABLE 5

| Outlet buffer tray configuration | | | | | | |
|---|---|---|---|---|---|---|
| No. | A | B | C | D | E | F |
| 6 | $H_2O$ (Cycle 24-35) | $H_2O$ (Cycle 24-35) | | | | |
| 5 | $H_2O$ (Cycle 12-23) | $H_2O$ (Cycle 12-23) | | | | |
| 4 | $H_2O$ (Cycle 1-11) | $H_2O$ (Cycle 1-11) | | | | |
| 3 | $H_2O$ (Cycle 24-35) | Waste (Cycle 24-35) | Gel-S (Cycle 24-35) | Waste (Cycle 24-35) | Waste (Cycle 24-35) | Waste (Cycle 24-35) |
| 2 | $H_2O$ (Cycle 12-23) | Waste (Cycle 12-23) | Gel-S (Cycle 12-23) | Waste (Cycle 12-23) | Waste (Cycle 12-23) | Waste (Cycle 12-23) |
| 1 | $H_2O$ (Cycle 1-11) | Waste (Cycle 1-11) | Gel-S (Cycle 1-11) | Waste (Cycle 1-11) | Waste (Cycle 1-11) | Waste (Cycle 1-11) |

Al to A6—Water, used in dip step to clean capillary tip, 1.5 mL
B4 to B6—Water, used in dip step to clean capillary tip, 1.5 mL
B1 to B3—Water, waste vial for SDS-MW gel buffer rinse, 0.8 mL
Cl to C3—Gel-S (SDS-MW gel buffer), used for separation, 1.1 mL
Dl to D3—Water, waste vial for 0.1N NaOH rinse, 0.8 mL
El to E3—Water, waste vial for 0.1N HCl rinse, 0.8 mL
Fl to F3—Water, waste vial for Water rinse, 0.8 mL Based on number of samples, filled up the buffer tray (Inlet and Outlet). The system automatically replenishes all reagents through an increment of the buffer array tray after every eleven cycles or samples.

Injection Sequence: Table 6 below shows Injection sequence:

| Sr. No. | Sample name | Runtime |
|---|---|---|
| | Conditioning | 10 |
| 1 | Blank | 30 |
| 2 | MW Standard | 30 |
| 3 | Test Sample-1 | 30 |
| | Conditioning | 10 |
| n-1 | Test Sample-n (n ≤ 12) | 30 |
| n | MW Standard (after every 10 samples and end of the sequence) | 30 |

Bracketing with MW standard was not required up to 5 samples. Samples include MW standard, blanks and test samples.

Separation of protein molecular weight size standard as shown in FIGS. 3 and 4.

Result: It is evident from FIG. 4 that using CE-SDS method the pancreatic protein extracted with citrate phosphate buffer shows the batch to batch consistency.

Example 4: Estimation of Protein by Using RP-HPLC

RP-HPLC is used to evaluate the qualitative attribute, indicating protein identity between reference and samples. Therefore, the chromatographic profile obtained should be reported, without any integration (Refer FIGS. 5 and 6).

Materials and reagent details: Water, Acetonitrile, TFA, DTT, Citric Acid, Na2HPO4, and HCl.

The Procedure for estimation of protein by using RP-HPLC:

1. Preparation of diluent buffer e.g., 100 Mm Citrate Phosphate Buffer mentioned above.
2. Mobile Phase Preparation: i) Mobile Phase A: 0.1% TFA in Water: Added 1.0 mL of TFA in 1000 mL of purified water. Mixed it well and sonicated for 5 minutes. ii) Mobile Phase B: 0.1% TFA in Acetonitrile: Added 1.0 mL of TFA in 1000 mL of Acetonitrile. Mixed it well and sonicated for 5 minutes.
3. Preparation of 1 M DTT: Weighed 154.3 mg of DTT and dissolved it in 1.0 mL of purified water. Mixed well. Prepared fresh every time.
4. Preparation of Pancrelipase test sample: For the extraction of proteins referred method for protein extraction and estimation for pancrelipase given above. Protein concentration value for pancrelipase extract is determined by BCA kit method. Considered this value for further dilution of non-reducing and reducing samples.

i. Non-Reducing Sample: Made the final concentration to 1.0 mg/m with the diluent buffer (100 mM Citrate Phosphate buffer).

ii. Reducing Sample: Diluted the sample to 1.0 mg/mL with purified water with a final DTT concentration of 10 mM in the sample. For this added 4 μL of 1 M DTT to 396 μL of 1 mg/mL sample. Incubated it for 30 minutes at 37° C. in water bath or dry bath. This sample is to be injected based on initial concentration to achieve final on-column load amount of 20 μg.

5. Method details for RP-HPLC:

Referred both the Tables 7 and Table 8 below for the details of chromatographic parameters.

TABLE 7

| Details of Chromatographic parameters | |
|---|---|
| Column description | Acquity BEH UPLC C18 column 2.1 × 150 mm, 1.7 μm, 300 Å |
| Column temperature | 70° C. |
| Sample manager temperature | 7° C. |
| Flow rate | 0.3 mL/min |
| Wavelength | 214 nm |

TABLE 8

Chromatography gradient details

| Time (min) | Mobile phase A (%) | Mobile phase B (%) | Flow (mL/min) | Curve |
|---|---|---|---|---|
| 0.0 | 100 | 0 | 0.3 | 6 |
| 3.0 | 100 | 0 | | |
| 18.0 | 70 | 30 | | |
| 20.0 | 63 | 37 | | |
| 50.0 | 55 | 45 | | |
| 65.0 | 25 | 75 | | |
| 70.0 | 0 | 100 | | |
| 75.0 | 0 | 100 | | |
| 76.0 | 100 | 0 | | |
| 80.0 | 100 | 0 | | |

Injection Sequence: 1) Injected one or two Blanks at the beginning of a sequence or till a stable baseline is achieved. 2) Injected reference standard solution before the injection of the first sample and at the end of a sequence.

Required Injected Blank and Injection sequence are given below in Table 9.

| Sr. No. | Solution | No. of injection |
|---|---|---|
| 1 | Blank (Mobile phase A) | 2 |
| 2 | Citrate phosphate buffer | 1 |
| 3 | Reference standard solution | 1 |
| 5 | Blank | 1 |
| 6 | Sample 1 | 1 |
| 7 | Sample 2 | 1 |
| 8 | Sample 3 | 1 |
| 9 | Blank | 1 |
| 10 | Reference standard solution Bracketing | 1 |

Results are shown in FIGS. 5 and 6. Data reporting and interpretation shown FIGS. 7 and 8.

FIG. 5 indicates that the various proteins present in the pancreatic protein extracted with citrate phosphate buffer are identified under non-reducing condition by RPC.

FIG. 6 indicates that the various proteins present in the pancreatic protein extracted with citrate phosphate buffer are identified under reducing condition by RPC.

It is evident from FIG. 7 that the pancreatic protein extracted with citrate phosphate buffer shows the batch to batch consistency.

It is evident from FIG. 8 that the pancreatic protein extracted with citrate phosphate buffer shows the batch to batch consistency.

Comparative hydrophobicity based qualitative profile of the constituent proteins obtained through reduced and non-reduced reverse phase chromatography need to be represented in the form of an overlay (FIGS. 7 and 8). Similarity between protein profiles observed between Reference standard and the samples needs to be inferred.

The invention claimed is:

1. A process for an extraction of a pancreatic protein from a pancreatic protein sample, the process comprising:

a. treating the pancreatic protein sample with a buffer;

b. dissolving the pancreatic protein sample in the buffer;

c. collecting the extracted pancreatic protein, wherein the suitable buffer is selected from citrate-phosphate buffer and bicarbonate buffer;

wherein the pancreatic protein sample comprises a pharmaceutical composition comprising:

one or more enzymes selected from lipase, protease, and amylase; and one or more enzymes selected from Triacylglycerol lipase, Co-lipase, CEL lipase, Phospholipase A2, Trypsin, Chymotrypsin, Elastase, Carboxypeptidase A1, Carboxypeptidase B, Kallikrien glandular, and Alpha amylase.

2. The process according to claim 1, wherein the extraction of the pancreatic protein is improved in comparison to an extraction process performed without using a suitable buffer selected from citrate-phosphate buffer and bicarbonate buffer.

3. The process according to claim 1, wherein:

the citrate-phosphate buffer concentration is selected from about 10 mM to about 200 mM; or the bicarbonate buffer concentration is selected from about 10 mM to about 200 mM.

4. The process according to claim 3, wherein:

the citrate-phosphate buffer concentration is selected from about 100 mM; or the bicarbonate buffer concentration is selected from about 100 mM.

5. The process according to claim 1, wherein the citrate phosphate buffer has a pH from about 6.0 to about 6.5.

6. The process according to claim 1, wherein of the bicarbonate buffer has a pH from about 9.5 to about 10.

7. The process according to claim 1, wherein dissolving the pancreatic protein sample in the buffer is performed by stirring or shaking.

8. The process according to claim 7, wherein stirring is performed at 200 rpm to 300 rpm.

9. The process according to claim 8, wherein stirring is performed for about 20 minutes to about 30 minutes.

10. The process according to claim 1, wherein the extracted pancreatic protein is further subjected to estimation of protein performed by using BCA, SDS-PAGE, CE-SDS, SE-HPLC, or RP-HPLC.

11. The process according to claim 1, wherein the extracted pancreatic protein is further subjected to quantification of protein performed by using SDS-PAGE, CE-SDS, SE-HPLC, or RP-HPLC.

12. The process according to claim 1, wherein the process provides more than about 80% yield of pancreatic protein.

13. The process according to claim 1, wherein the process provides more than about 90% yield of pancreatic protein.

14. The process according to claim 1, wherein the process provides more than about 98% yield of pancreatic protein.

15. The process according to claim 1, wherein the extracted pancreatic protein comprises a protein selected from amylase, lipase and protease.

16. The process according to claim 1, wherein the process provides a pharmaceutically acceptable pancreatic protein mixture comprising one or more enzymes selected from amylase, lipase and protease.

17. The process according to claim 10, wherein the extracted pancreatic protein is further subjected to estimation of protein based on molecular weight by using CE-SDS.

18. The process according to claim 10, wherein the extracted pancreatic protein is further subjected to estimation of purity profile by using RP-HPLC.

19. The process according to claim 10, wherein the extracted pancreatic protein is further subjected to estimation of protein based on molecular weight by using SDS-PAGE.

20. The process according to claim 10, wherein the extracted pancreatic protein is further subjected to estimation of purity profile by using SE-HPLC.

* * * * *